United States Patent
Chun et al.

(10) Patent No.: US 9,346,054 B2
(45) Date of Patent: May 24, 2016

(54) NON-CONTACT HEATING TYPE OF GENE AMPLIFICATION SYSTEM

(75) Inventors: Hyang Sook Chun, Seoul (KR); Sung Wook Choi, Suwon-si (KR); Na Ri Lee, Seoul (KR); Hyun Joo Chang, Seoul (KR)

(73) Assignee: KOREA FOOD RESEARCH INSTITUTE, Seongnam-si, Gyeonggi-do (KR)

( * ) Notice: Subject to any disclaimer, the term of this patent is extended or adjusted under 35 U.S.C. 154(b) by 304 days.

(21) Appl. No.: 13/824,323

(22) PCT Filed: Nov. 15, 2010

(86) PCT No.: PCT/KR2010/008059
§ 371 (c)(1),
(2), (4) Date: Mar. 15, 2013

(87) PCT Pub. No.: WO2012/036341
PCT Pub. Date: Mar. 22, 2012

(65) Prior Publication Data
US 2013/0177971 A1      Jul. 11, 2013

(30) Foreign Application Priority Data
Sep. 17, 2010   (KR) .................. 10-2010-0091771

(51) Int. Cl.
*B01L 7/00* (2006.01)
*C12Q 1/68* (2006.01)

(52) U.S. Cl.
CPC .............. *B01L 7/52* (2013.01); *B01L 7/5255* (2013.01); *B01L 2300/0803* (2013.01); *B01L 2300/0829* (2013.01); *B01L 2300/168* (2013.01); *B01L 2300/1844* (2013.01);

(Continued)

(58) Field of Classification Search
CPC .......... B01L 7/00; B01L 7/52; B01L 7/5255; B01L 2300/0803; B01L 2300/0829; B01L 2300/1861; B01L 2300/1872; C12Q 1/6844
See application file for complete search history.

(56) References Cited

U.S. PATENT DOCUMENTS

| | | | | |
|---|---|---|---|---|
| 5,525,300 A | * | 6/1996 | Danssaert et al. | 422/552 |
| 5,639,428 A | * | 6/1997 | Cottingham | 422/112 |
| 6,269,551 B1 | * | 8/2001 | Imada et al. | 34/266 |

(Continued)

FOREIGN PATENT DOCUMENTS

| | | |
|---|---|---|
| KR | 1020090133079 A | 12/2009 |
| KR | 1020100008476 A | 1/2010 |
| WO | WO 2009067744 A1 * | 6/2009 |

OTHER PUBLICATIONS

English language machine translation of the Abstract, Karaki et al., "JP 60137277A", 1985, translated Nov. 7, 2014.*

(Continued)

*Primary Examiner* — Michael Hobbs
*Assistant Examiner* — Liban Hassan
(74) *Attorney, Agent, or Firm* — Novick, Kim & Lee, PLLC; Jae Youn Kim (57) ABSTRACT

Disclosed is a non-contact heating type gene amplification system. The non-contact heating type gene amplification system includes separate light sources for each step of a polymerase chain reaction in order to perform a high-speed temperature cycle by moving a rotation unit, in which a plurality of sample chambers are formed, to places at which the sample chambers are controlled at the temperatures corresponding to each step.

5 Claims, 8 Drawing Sheets

(52) U.S. Cl.
CPC . *B01L 2300/1861* (2013.01); *B01L 2300/1872* (2013.01); *C12Q 1/6844* (2013.01)

(56) References Cited

U.S. PATENT DOCUMENTS

| | | | |
|---|---|---|---|
| 2004/0131345 A1* | 7/2004 | Kylberg et al. | 392/465 |
| 2005/0287661 A1 | 12/2005 | Landers | |
| 2006/0073584 A1* | 4/2006 | Sasaki et al. | 435/288.5 |
| 2006/0192470 A1* | 8/2006 | Bonnin et al. | 313/25 |
| 2008/0176230 A1 | 7/2008 | Owen et al. | |
| 2008/0199370 A1* | 8/2008 | Mourtada et al. | 422/186.04 |
| 2008/0227191 A1* | 9/2008 | Tsukada | 435/308.1 |
| 2009/0226903 A1* | 9/2009 | Cobb | 435/6 |

OTHER PUBLICATIONS

Sudip Mondal et al. Novel fluorescence detection technique for non-contact temperature sensing in microchip PCR. J. Biochem. Biophys. Methods. 2007, vol. 70, Issue 5, pp. 773-777.

Sudip Mondal et al. In situ monitoring of polymerase extension rate and adaptive feedback control of PCR by using fluorescence measurements. J. Biochem. Biophys. Methods. 2005, vol. 65, Issue 2-3, pp. 97-105.

* cited by examiner

NON-CONTACT HEATING TYPE OF GENE AMPLIFICATION SYSTEM

TECHNICAL FIELD

The present invention relates to a non-contact heating type gene amplification system, and more particularly, to a non-contact heating type gene amplification system which includes separate light sources for each step of a polymerase chain reaction in order to perform a high-speed temperature cycle by moving a rotation unit, in which a plurality of sample chambers are formed, to places at which the sample chambers are controlled at the temperatures corresponding to each step.

BACKGROUND ART

Recently, as molecular biology has been rapidly developed, a genetic diagnosis technology has been developed more rapidly than a diagnosis using an antigen-antibody reaction or a biomolecular interaction.

The genetic diagnosis technology requires DNA replication and amplification for a rapid diagnosis. Kary Mullis, who is a biochemist in U.S.A., has proposed a PCR (Polymerase Chain Reaction) as one method for DNA replication and amplification.

Three steps of DNA denaturation, annealing and elongation are required to cause the PCR.

A thermal source is necessarily required since the higher temperature than the normal temperature must be maintained for the denaturation, annealing and elongation steps.

The thermal source for heating DNA may be classified into a contact type in which the thermal source makes direct contact with a sample chamber and a non-contact type in which the thermal source does not make direct contact with a sample chamber.

The contact type thermal source includes a heater using a Peltier device or resistance heat and the non-contact type thermal source utilizes near infrared ray, far infrared ray, hot air, or a magnetron as the thermal source.

The contact type thermal source indirectly heats the DNA received in a sample chamber by allowing the sample chamber to make contact with a heating block including a Peltier device or a resistance device, so that additional time is taken to transfer heat from the heating block serving as the thermal source to the DNA.

Meanwhile, in the non-contact type thermal source, the DNA received in the sample chamber is directed heated without making contact with a heat transfer medium. Since air is heated when hot air is used, a space for making the hot air is required. In a case of magnetron, a high frequency corresponding to a resonant frequency of water is generated to heat a target. In this case, although the target is heated at a high speed, a metal material which may exert a bad influence on the resonant frequency is not used around the thermal source, a large space for heating the target is required and an electromagnetic wave harmful to the human body is radiated.

In addition, although the target may be rapidly heated to the target temperature at a high speed and may be directly heated without an intermediate heat transfer medium when the infrared ray is used, time for changing the temperature of the heat source is required and the infrared ray is absorbed into most materials.

A high speed gene amplification apparatus for causing a PCR using the infrared ray according to the related art is disclosed in US patent publication No. 2005/0287661. The amplification apparatus disclosed in the above patent document uses a single heat source to control the temperatures corresponding to the denaturation, annealing and elongation steps in the same chamber.

However, since the gene amplification apparatus for causing the PCR according to the related art uses the single heat source, a considerable amount of time is spent until the temperature of the sample chamber heated at the high temperature drops.

In addition, since the signal heat source is used, the temperature is not actively changed corresponding to each step, so it is impossible to amplify a plurality of gene samples in various conditions.

DISCLOSURE

Technical Problem

The present invention has been made to solve the problems occurring in the prior art, and an object of the present invention is to provide a non-contact heating type gene amplification system which includes separate light sources for each step and can perform a high speed temperature cycling by separately controlling the temperatures of each step.

Another object of the present invention is to provide a non-contact heating type gene amplification system which can amplify a plurality of gene samples in various conditions by separately controlling the temperatures corresponding to each step.

Another object of the present invention is to provide a non-contact heating type gene amplification system which includes a rotation unit in which a sample chamber including a material having a suitable optical property to effectively transfer infrared ray light to a sample is formed, so that heat is transferred to the gene sample at a high speed.

Another object of the present invention is to provide a non-contact heating type gene amplification system, in which a rotation unit includes a material having superior optical characteristics where one side surface of the rotation unit, to which light radiates from a light source, is formed of glass transmitting the infrared ray and an opposite surface of the rotation unit, to which the light does not radiate from the light source, is formed of plastic absorbing the infrared ray, so that the heating efficiency is more improved.

Another object of the present invention is to provide a non-contact heating type gene amplification system which improves cooling efficiency by forming a non-heating unit between the denaturation unit for performing the denaturation step and the annealing unit for performing the annealing step.

Another object of the present invention is to provide a non-contact heating type gene amplification system which includes a separate cooling unit to forcibly drop the temperature of the non-heating unit, so that the cooling efficiency is more improved.

Another object of the present invention is to provide a non-contact heating type gene amplification system which includes a temperature sensor and a control panel for controlling the system through the temperature sensor, so that a polymerase chain reaction is more effectively caused.

Another object of the present invention is to provide a non-contact heating type gene amplification system in which the control panel performs a PID control according to the signal transferred from the temperature sensors, so that the temperature can stably and easily reach the target temperature.

Another object of the present invention is to provide a non-contact heating type gene amplification system which includes a light condensing unit for condensing the light from the light source and a diaphragm for controlling an area on which the light is irradiated, so that the sample can be rapidly heated, thereby improving the thermal efficiency.

Another object of the present invention is to provide a non-contact heating type gene amplification system which includes a filter for filtering visible rays installed on a lower portion of the sample chamber to quantitatively detect a DNA by additionally installing an optical detector such as a fluorescence detector as necessary.

Technical Solution

In order to accomplish the objects of the present invention, there is provided a non-contact heating type gene amplification system for amplifying a gene through denaturation, annealing and extension steps, where temperatures in each of the denaturation, annealing and extension steps are controlled through separate light source modules and the gene is amplified by a rotation of a rotation unit, in which a plurality of sample chambers are formed at places corresponding to locations of the light sources.

The light source modules are provided in a circumference direction and a number of the light source modules is a multiple of 3.

Preferably, the light source module includes a halogen lamp.

Preferably, the halogen lamp is deposited thereon with ruby or gold.

Preferably, the sample chambers are symmetrically formed in a circumference direction of the rotation unit about a center of the rotation unit and a number of the sample chambers is a multiple of 4.

Preferably, the rotation unit has one side surface, which is formed of glass transmitting infrared ray and to which light radiates from a light source, and an opposite surface, which is formed of plastic absorbing infrared ray and to which the light is not radiated from the light source.

Preferably, a denaturation unit to perform the denaturation step, an annealing unit to perform the annealing step, an elongation unit to perform the extension step, and a non-heating unit formed between the denaturation unit and the annealing unit and having no separate light source are prepared in a form of a cycle.

Preferably, the non-heating unit includes a separate cooling unit to forcibly drop a temperature.

Preferably, the non-contact heating type gene amplification system further includes temperature sensors formed over the sample chambers; and a control panel to PID control operations of the light source module, a cooling unit and the rotation unit according to a preset program by calculating signals transferred from the temperature sensors, wherein the rotation unit is formed over the denaturation unit, the annealing unit and the extension unit and includes the sample chambers into which DNAs are injected.

Preferably, the light source module includes a light source to irradiate light; a light condensing unit to condense the light from the light source by reflecting the light; and a diaphragm to control an area on which the light is irradiated.

Preferably, the non-contact heating type gene amplification system further includes a filter installed on a lower portion of the sample chamber to filter visible light in order to examine a DNA received in the sample chamber.

Preferably, a fluorescence detector is installed on an upper end of the sample chamber to quantitatively detect a gene.

BEST MODE

Mode for Invention

Hereinafter, a non-contact heating type gene amplification system according to the embodiment will be described as follows.

The non-contact heating type gene amplification system controls denaturation, annealing and extension steps which constitute each step of polymerase chain reaction, respectively. Thus, the non-contact heating type gene amplification system controls the times and temperatures of each step according to the preset condition such that temperature cycling may be implemented.

Figure 1:
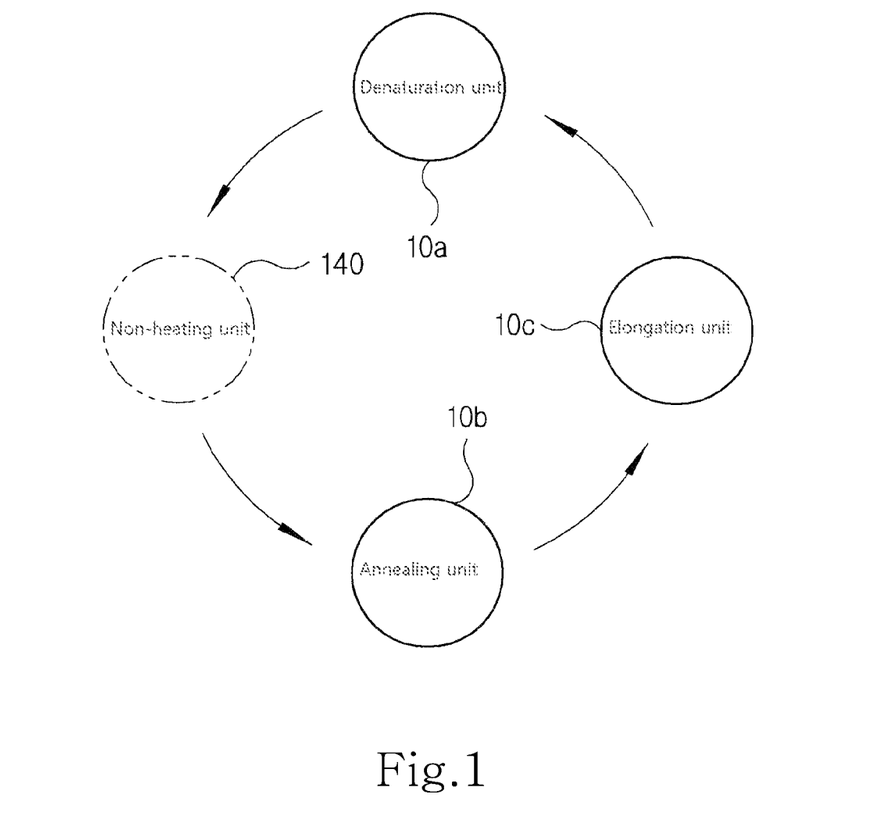
FIG. 1 is a conceptual diagram schematically showing a non-contact heating type gene amplification system according to an embodiment of the present invention.
Figure 2:
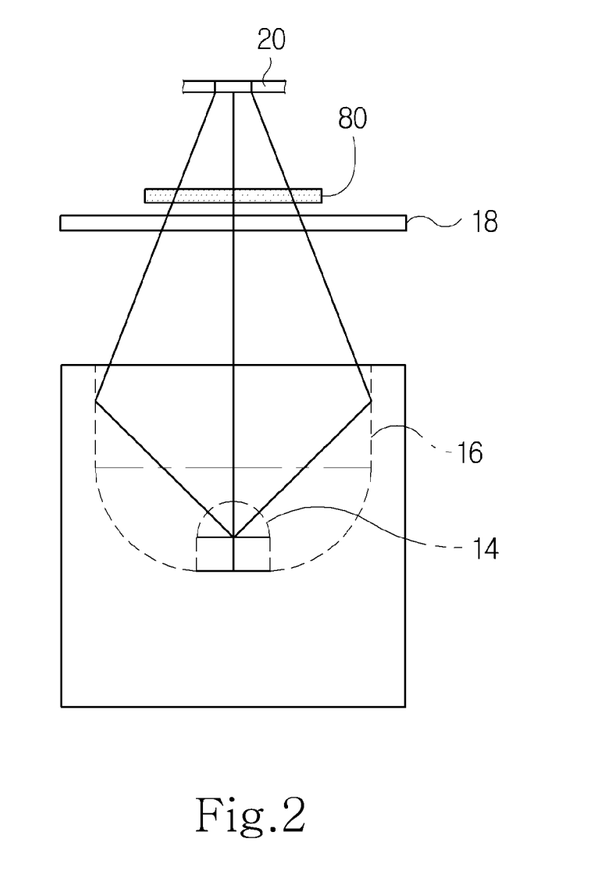
FIG. 2 is a conceptual diagram schematically showing a light condensing scheme of a non-contact heating type gene amplification system according to an embodiment of the present invention.

As shown in FIG. 1, the non-contact heating type gene amplification system includes a denaturation unit 10a for performing the denaturation step, an annealing unit 10b for performing the annealing step and the elongation unit 10c for performing the extension step such that a cycle is implemented. As shown in FIG. 2, light source modules 12 are installed in the denaturation unit 10a, the annealing unit 10b and the elongation unit 10c, respectively. Thus, the temperatures of the denaturation unit 10a, the annealing unit 10b and the elongation unit 10c are controlled individually, so that the high-speed temperature cycling may be implemented.

In addition, the non-contact heating type gene amplification system preferably includes a non-heating unit 140 formed between the denaturation unit 10a, and the annealing unit 10b. The non-heating unit 140 does not include an additional light source in order to perform a cooling step as a rest period for dropping the high temperature in the denaturation step to the low temperature for performing the annealing step.

Figure 3:
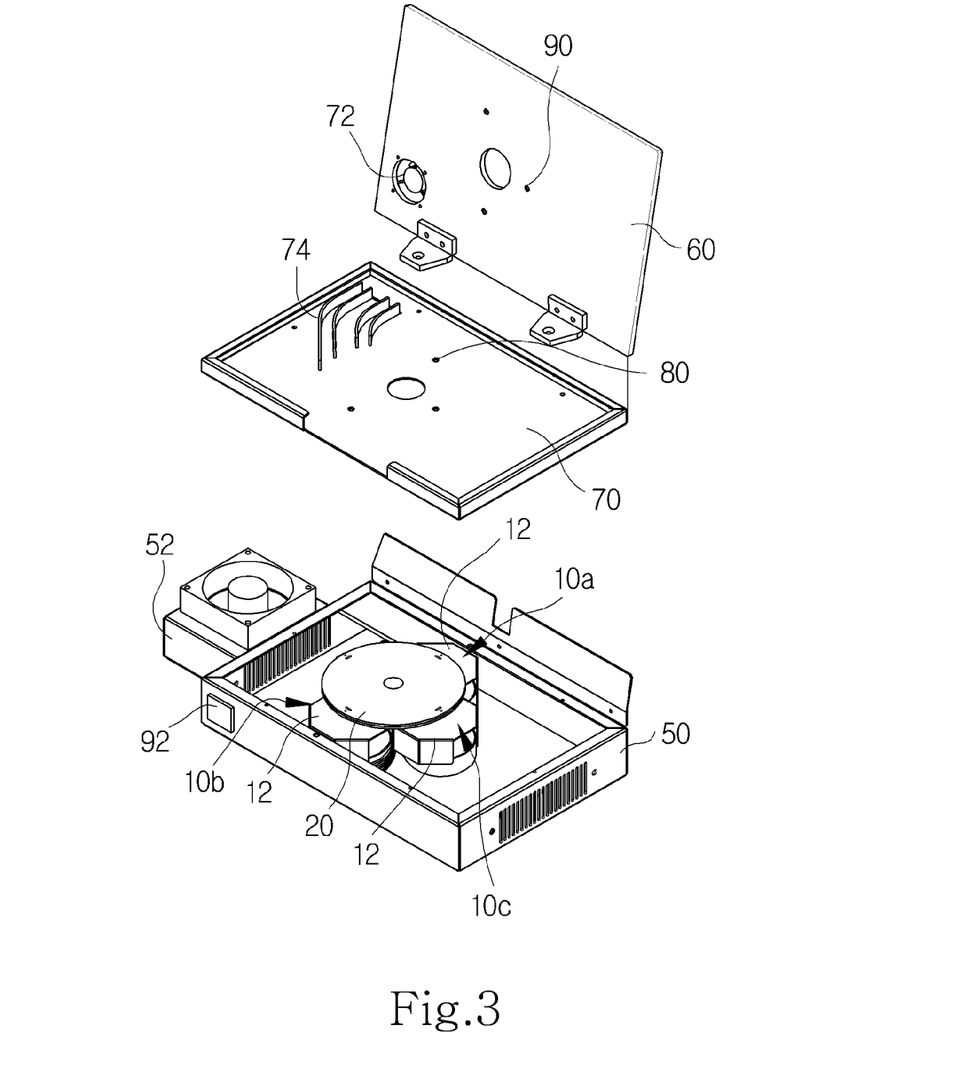
FIG. 3 is an exploded perspective view showing a non-contact heating type gene amplification system according to an embodiment of the present invention.
Figure 4:
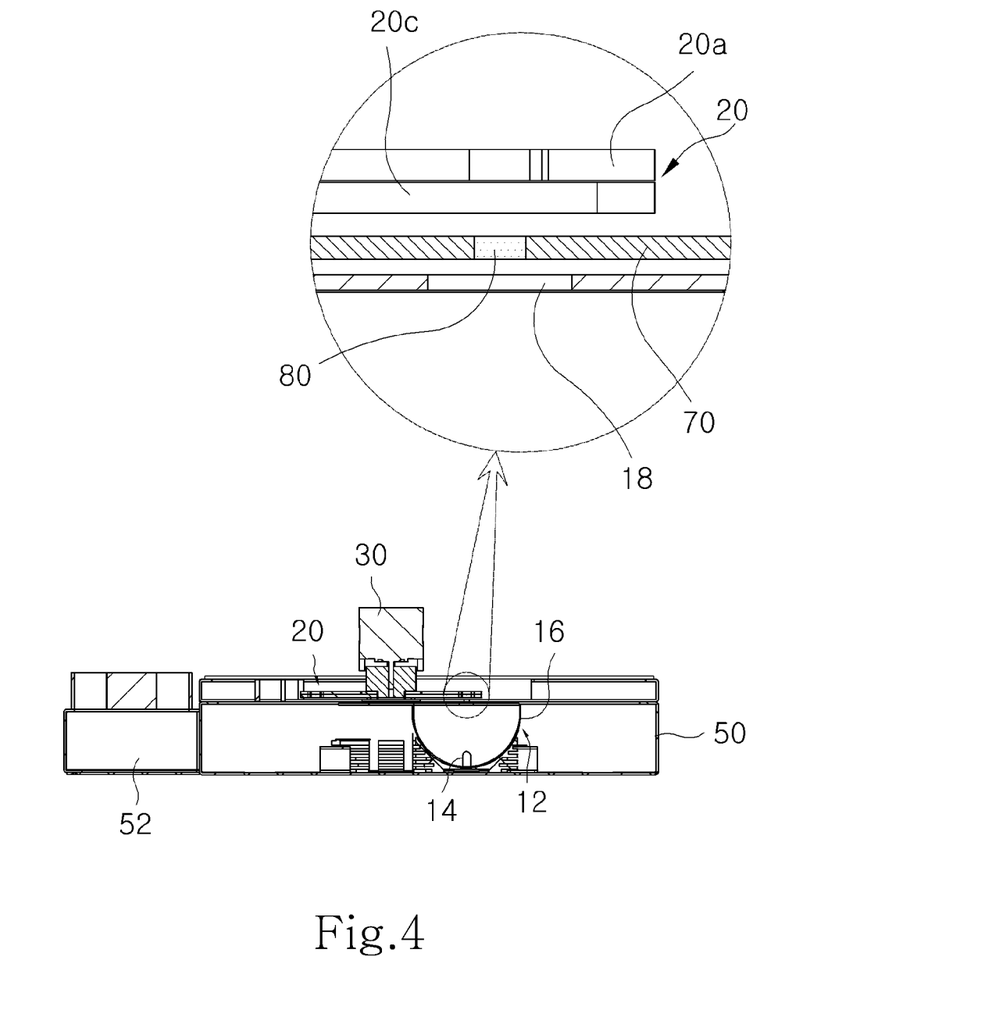
FIG. 4 is a sectional view showing a non-contact heating type gene amplification system according to an embodiment of the present invention.

As shown in FIGS. 1 to 3, the non-contact heating type gene amplification system further includes a rotation unit 20 having a plurality of sample chambers 22 into which DNAs are injected and which are formed over the denaturation unit 10a, the annealing unit 10b and the elongation unit 10c, temperature sensors 90 formed over the sample chambers 22, and a control panel 92 for calculating signals from the temperature sensors 90 in order to PID controlling the light sources 12, the cooling unit and the rotation unit 20 according to a preset program. Thus, since each step is performed to amplify genes while the rotation unit 20 in which the plurality of sample chambers 22 are formed is being rotated, a plurality of genes may be simultaneously amplified. Further, the temperatures are sensed by the temperatures sensors 90 and the operations of the light source modules 12, the cooling unit and the rotation unit 20 are controlled by the preset program, so that the polymerase chain reaction is performed more effectively. In addition, since the control panel 92 performs the PID control according to the signal transferred from the temperature sensors 90 thereto, the temperature may reach stably and easily the target temperature.

Further, the light source module 12 includes a light source 14 for irradiating light, a light condensing unit 16 for condensing the light from the light source 14 by reflecting the light, and a diaphragm 18 for controlling an area on which the light is irradiated. Thus, since the area irradiated through the diaphragm 18 may be limited, the samples may be rapidly heated so that the thermal efficiency may be improved. In addition, a filter 80 is installed over the diaphragm 18 placed at the sample chamber 22 to filter visible light in order to examine a DNA received in the sample chamber 22. Since the filter 80 cuts off visible light, when a fluorescence detector (not shown) is additionally installed, the DNA received in the sample chamber 22 may be detected without light interference by the light source.

In detail, as shown in FIGS. 1 to 6, the non-contact heating type gene amplification system according to the embodiment is formed in a concentric circle form, and includes the denaturation, annealing and elongation units 10a, 10b and 10c which include the light module 12, respectively, the non-heating unit 140 formed between the denaturation and annealing units 10a and 10b, the rotation unit 20 which is installed to be rotated on the denaturation, annealing and elongation unit 10a, 10b and 10c.

First, the denaturation, annealing and elongation units 10a, 10b and 10c are formed to perform each step of a polymerase chain reaction. Although the light sources are installed one by one on the denaturation, annealing and elongation units 10a, 10b and 10c, if necessary, the units 10a, 10b and 10c and the light sources of a multiple of 3 may be installed. The non-heating unit 140 is formed between the denaturation and annealing units 10a and 10b. Thus, the denaturation, annealing, elongation and non-heating units 10a, 10b, 10c and 140 are preferably spaced apart from each other by 90° in the form of the concentric circle.

The light source module 12 includes the light source for irradiating light, a light condensing unit 16 for condensing the light from the light source 14 by reflecting the light, and a diaphragm 18 for controlling an area on which the light is irradiated.

As shown in FIG. 2, the light irradiated from the light source 14 is condensed at the light condensing unit 16 and then, goes toward the diaphragm 18. After the light condensed at the diaphragm 18 passes through the filter 80, the light heats the sample chamber 22 of the rotation unit 20.

The light source 14 includes the halogen lamp on which ruby is deposited. If necessary, gold may be deposited the light source 14, as well as ruby. In addition, if necessary, any other lamp, which can irradiate infrared ray or particularly, near infrared ray, may be used for the light source, as well as the halogen lamp.

The light condensing unit 16 includes a mirror having a parabola shape and formed of aluminum at a lower portion of the light source 14. The light condensing unit 16 condenses the light generated from the light source 14 and transfers the condensed light to a target.

The diaphragm 18 is installed to adjust the area of light irradiated upward after the light is condensed by the light condensing unit 16. In the embodiment, although the diaphragm 18 includes a hole having a circular shape, the diaphragm 18 may be configured to allow the area of the diaphragm to be variable. According to the embodiment, the light source module 12 is installed and fixed into a housing 50 having an opened top surface. A power supply unit (not shown) for applying a power to the light source 14 as well as the light source module 12 is installed in the housing 50. A cooling fan 52 for cooling the inner space of the housing 50 is installed at one side of the housing 50.

The rotation unit 20 is located over the denaturation, annealing and elongation units 10a, 10b and 10c and the plurality of sample chambers 22 into which DNAs are injected are formed along a circumference direction in the rotation unit 20. The sample chambers 22 are formed at the places corresponding to the places of the denaturation, annealing and elongation units 10a, 10b and 10c, and the non-heating unit 140. The sample chambers 22 are symmetrically formed in the circumference direction about the center of the rotation unit 20 and the number of the sample chambers 22 is a multiple of 4.

Figure 5:
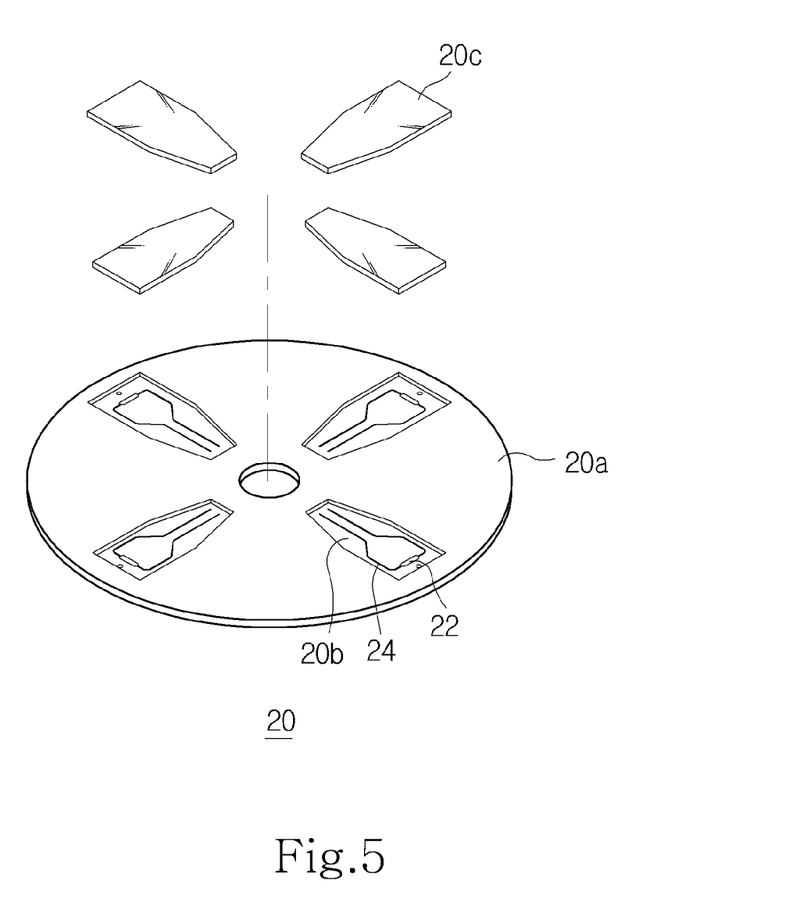
FIG. 5 is an exploded perspective view showing a rotation unit of a non-contact heating type gene amplification system according to an embodiment of the present invention when the rotation unit is viewed from the bottom.
Figure 6:
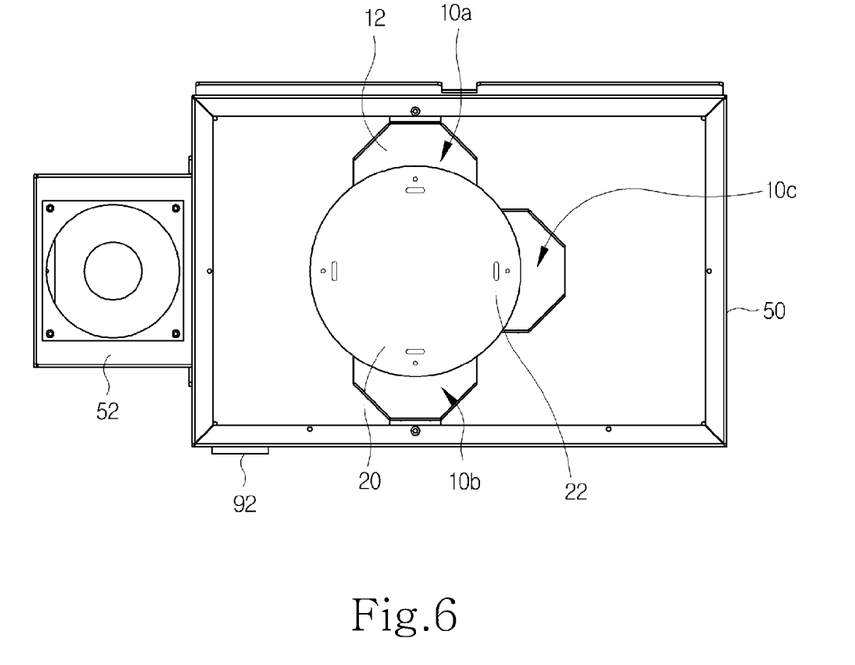
FIG. 6 is a plane view showing a non-contact heating type gene amplification system from which a cover is removed according to an embodiment of the present invention.

The rotation unit 20 includes a base plate 20a having a disc shape and a cover plate 20c which is fitted into a recess 20b of base plate 20a. The base plate 20a is formed of infrared ray absorbing plastic and the recess 20b having the sample chamber 22 is formed in the base plate 20a. Thus, the recesses 20b are formed at the places corresponding to the denaturation, annealing and elongation units 10a, 10b and 10c, and the non-heating unit 140. Preferably, the cover plates 20c which are fitted into the recesses 20c are formed of infrared ray transmitting glass, respectively. Thus, the light generated from the light source passes through the glass so that the light heats the sample chambers 22.

Each sample chamber 22 has an ellipse shape and is formed in the recesses 22b of the rotation unit and a fine flow path 24 is formed at both sides of each sample chamber 22 such that a DNA sample flows in the sample chamber 22 therethrough. The DNA samples flow into each of the sample chambers 22 along the fine flow paths 24 by a capillary phenomenon.

The rotation unit 20 is rotated by a driving motor 30. Preferably, a stepping motor is used as the driving motor 30 in order to rotate the rotation unit 20 at a predetermined angle. The driving motor 30 is mounted on the top plate 60 which is hinge coupled with the one side of the housing 50. In addition, a middle plate 70 is installed at the lower portion of the rotation unit 20. Filters are installed at the places corresponding to the sample chambers 22. The filters 80 filter visible ray so that DNA diagnoses may be easily performed in examination.

In addition, temperature sensors 90 are installed at corresponding places on the cover 60 over the sample chambers 22. The sensing signals of the temperature sensors 90 are transferred to the control panel 92.

The cooling unit includes a fan 72 mounted on the cover 60, and an air path 74 formed on the middle plate 70 below the cover 60 and having a rear end directly placed under the fan 72 and a front end extending to the non-heating unit. Thus, external air is introduced through the fan 72 and then introduced into the non-heating unit through the air path 74.

The control panel 92 calculates the signals transferred from temperature sensors 90 and controls the light source module 12, the cooling unit and the rotation unit 30 according to the preset program.

Preferably, the control panel 92 performs a PID control by using the signals from the temperature sensors 90. As the PID control basically is a form of a feedback controller, the PID control measures an output value from the temperature sensors 90 and sets new output values necessary for control by using a calculated error value, so that the temperature can reach stably and easily the target temperature.

Figure 7:
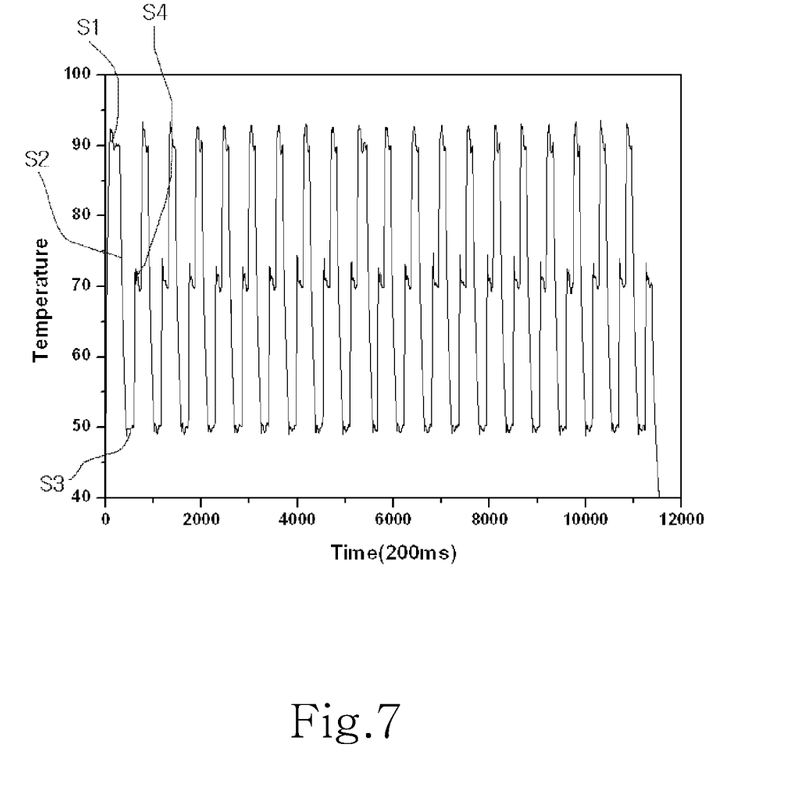
FIG. 7 is a graph illustrating a temperature cycling of a non-contact heating type gene amplification system according to an embodiment of the present invention.

As shown in FIG. 7, the control panel controls such that the temperature cycle is implemented through the denaturation, annealing and elongation steps S1, S2 and S3. In the embodiment, the temperature cycle implemented through the steps includes 20 cycles.

Figure 8:
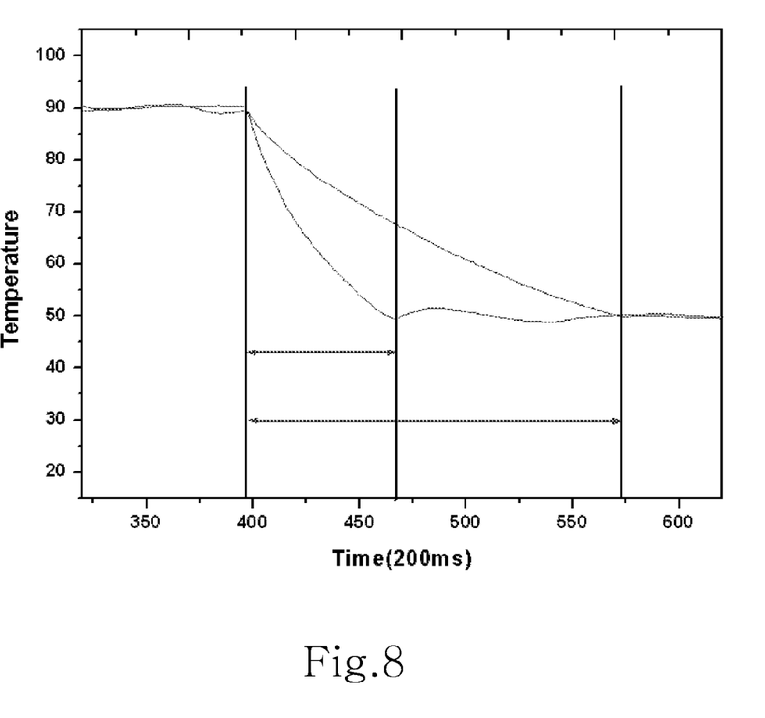
FIG. 8 is a graph showing a temperature gradient before and after a cooling unit is installed in a non-contact heating type gene amplification system according to an embodiment of the present invention.

Further, when the control panel does not perform the cooling step known in the art as shown in FIG. 8, although the time which is taken from the denaturation temperature to the annealing temperature is excessively spent, when the cooling step S2 of the embodiment is included, the sample is cooled at the cooling speed twice as fast as that of the art so that the spent time is reduced from 35 seconds to 14 seconds. Thus, it is known that a substantial amount of time difference exists according to whether the cooling step S2 is performed. Therefore, according to the embodiment, since the embodiment includes the cooling step S2, the sample denaturized at a high temperature may be rapidly cooled so that the gene may be amplified at a high speed.

As shown in FIG. 7, the non-contact heating type gene amplification system according to the embodiment describe above, includes the denaturation step S1 of denaturizing the sample in the sample chamber 22, the cooling step S2 of cooling the sample in the sample chamber 22, the annealing step S3 of annealing the sample in the sample chamber 22, and the extension step S4 of extending the sample in the sample chamber 22.

First, the temperature of the sample is maintained in the range of 90° C. to 97° C. by irradiating light of the light source module 12 onto the sample chamber 22 in the denaturation step S1. In the denaturation step S1, the control panel 92 performs the PID control by using the signal from the temperature sensor 90 so that the set temperature of the sample is maintained. The control panel 92 controls the driving motor 30 according to the preset program so that the rotation unit 20 is rotated by 90° after a predetermined time is elapsed, so the sample is transferred for the next step.

Next, in the cooling step S2, the sample of which the temperature is maintained in the range of 90° C. to 97° C. is cooled to the temperature required for the annealing step S3 in the range of 50° C. to 65° C. The control panel 92 controls the fan 72 such that the temperature of the sample drops. The control panel 92 controls the driving motor 30 according to the preset program so that the rotation unit 20 is rotated by 90° after the predetermined time is elapsed, so the sample is transferred for the next step.

Next, in the annealing step S3, the temperature of the sample cooled at the temperature in the range of 50° C. to 65° C. in the cooling step S2 is maintained at the temperature suitable for the annealing step in the range of 50° C. to 65° C. by irradiating the light from the light source module 12 onto the sample. In the annealing step S3, the control panel 92 performs the PID control by using the signal from the temperature sensor 90 so that the set temperature of the sample is maintained. The control panel 92 controls the driving motor 30 according to the preset program so that the rotation unit 20 is rotated by 90° after a predetermined time is elapsed, so the sample is transferred for the next step.

Next, in the extension step S4, the temperature of the sample maintained at the temperature in the range of 50° C. to 65° C. in the annealing step S3 is increased at the temperature suitable for the extending step S4 in the range of 68° C. to 74° C. by irradiating the light from the light source module 12 onto the sample. In the extension step S4, the control panel 92 performs the PID control by using the signal from the temperature sensor 90 so that the set temperature of the sample is maintained. The control panel 92 controls the driving motor 30 according to the preset program so that the rotation unit 20 is rotated by 90° after a predetermined time is elapsed, so the sample is transferred for the next step.

INDUSTRIAL APPLICABILITY

As described above, the non-contact heating type gene amplification system according to the present invention includes separate light sources for each step and can perform a high speed temperature cycling by separately controlling the temperatures of each step.

The non-contact heating type gene amplification system according to the present invention can amplify various samples by separately controlling the temperatures corresponding to each step.

The non-contact heating type gene amplification system according to the present invention improves cooling efficiency by forming a non-heating unit between the denaturation unit for performing the denaturation step and the annealing unit for performing the annealing step.

The non-contact heating type gene amplification system according to the present invention includes a separate cooling unit to forcibly drop the temperature of the non-heating unit, so that the cooling efficiency can be more improved.

The non-contact heating type gene amplification system according to the present invention includes a temperature sensor and a control panel for controlling the system through the temperature sensor, so that a polymerase chain reaction can be more effectively caused.

The non-contact heating type gene amplification system according to the present invention includes the control panel which performs the PID control according to the signal transferred from the temperature sensors, so that the temperature may stably and easily reach the target temperature.

The non-contact heating type gene amplification system according to the present invention includes a light condensing unit for condensing the light from the light source and a diaphragm for controlling an area on which the light is irradiated, so that the sample can be rapidly heated.

The non-contact heating type gene amplification system according to the present invention includes a filter for filtering visible rays installed on a lower portion of the sample chamber to quantitatively detect a DNA by installing an optical detector such as a fluorescence detector as necessary.

The non-contact heating type gene amplification system according to the present invention includes the rotation unit which has one side surface, which is formed of glass transmitting infrared ray and to which light radiates from the light source, and an opposite surface, which is formed of plastic absorbing infrared ray and to which the light does not radiate from the light source, so that the heating efficiency of the sample chamber is improved.

The invention claimed is:

1. A non-contact heating gene amplification system for amplifying a gene through denaturation, annealing and extension steps, the non-contact heating gene amplification system comprising:
   a denaturation unit to perform the denaturation step;
   an annealing unit to perform the annealing step;
   an elongation unit to perform the extension step;
   a plate disposed above the denaturation unit, the annealing unit, and the elongation unit;
   a cover disposed on the plate; and
   a plurality of light source modules, each of the plurality of light source modules comprising:
   a light source for radiating light, the light source having a halogen lamp;
   a light condensing unit to condense the light from the light source by reflecting the light; and
   a diaphragm to adjust an area on which the light is irradiated;
   a rotation unit interposed between the plate and the cover, the rotation unit having a plurality of sample chambers; and
   a filter installed on a lower portion of the plurality of sample chambers to filter visible light in order to examine a DNA received in the plurality of sample chambers,
   wherein the non-contact heating gene amplification system further comprises a non-heating unit disposed between the denaturation unit and the annealing unit, wherein the non-heating unit includes a cooling unit and an air path, wherein the cooling unit comprises a fan mounted on the cover,
   wherein the air path is defined on the plate and the air path has one end directly placed below the fan,
   wherein each of the denaturation unit, the annealing unit and the extension unit has one of the plurality of light source modules, respectively,
   wherein the halogen lamp is deposited thereon with ruby or gold, and wherein the gene is amplified by a rotation of the rotation unit, in which the plurality of sample chambers are disposed at places corresponding to locations of the light source.

2. The non-contact heating gene amplification system of claim 1, wherein the light source is disposed along a circumferential direction of the rotation unit and a number of the light source modules is a multiple of three (3).

3. The non-contact heating gene amplification system of claim 1, wherein the plurality of sample chambers are symmetrically disposed along a circumferential direction of the rotation unit with respect to a center of the rotation unit and a number of the plurality of sample chambers is a multiple of four (4).

4. The non-contact heating gene amplification system of claim 1, wherein the rotation unit has a first side surface, which is comprised of glass material transmitting an infrared ray there-through and to which the light radiates from the light source, and a second side surface, which is formed of plastic material absorbing the infrared ray.

5. The non-contact heating gene amplification system of claim 1, further comprising:
   temperature sensors disposed above the plurality of sample chambers; and
   a control panel performing PID control operations to the plurality of light source modules, the cooling unit, and the rotation unit according to a preset program by calculating signals transferred from the temperature sensors.

* * * * *